United States Patent

Daum et al.

[11] 4,026,934
[45] May 31, 1977

[54] 1-TRIORGANO-STANNYL-3-SUBSTITUTED-2,4-DIOXO-1,2,3,4-TETRAHYDRO-s-TRIAZINO-[1,2-a]-BENZIMIDAZOLES

[75] Inventors: Werner Daum, Krefeld; Wolfgang Behrenz, Overath-Steinenbrueck; Ingeborg Hammann, Cologne; Hans Scheinpflug, Leverkusen; Wilhelm Brandes, Cologne, all of Germany

[73] Assignee: Bayer Aktiengesellschaft, Leverkusen, Germany

[22] Filed: June 4, 1976

[21] Appl. No.: 693,037

[30] Foreign Application Priority Data

June 26, 1975 Germany .......................... 2528623

[52] U.S. Cl. .................. 424/245; 260/242; 260/249.5; 260/299; 260/309.2
[51] Int. Cl.² .............. A61K 31/32; C07D 487/04
[58] Field of Search ........... 260/242, 299, 249.5; 424/245

[56] References Cited

UNITED STATES PATENTS

| | | | |
|---|---|---|---|
| 3,725,406 | 4/1973 | Bose et al. ............ | 260/249.5 |
| 3,764,678 | 10/1973 | Knusli et al. ............ | 424/245 |
| 3,907,818 | 9/1975 | Buchel et al. ............ | 260/299 |

OTHER PUBLICATIONS

Chemical Abstracts, vol. 78, Abst. No. 159686k (1973).
Chemical Abstracts vol. 79, Abst. No. 101526n (1973).
Capuano et al, Chem. Ber. vol. 107, pp. 62–67 (1974).

Primary Examiner—John D. Randolph
Attorney, Agent, or Firm—Burgess, Dinklage & Sprung

[57] ABSTRACT

1-Triorgano-stannyl-3-substituted-2,4-dioxo-1,2,3,4-tetrahydro-s-triazino-[1,2-a]-benzimidazoles of the formula

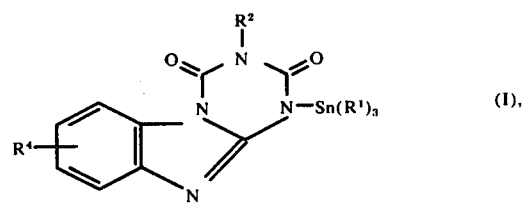

in which
$R^1$ is alkyl or cycloalkyl with 4 to 8 carbon atoms, or phenyl, and
$R^2$ is alkyl with 1 to 18 carbon atoms optionally substituted by chlorine, CN, alkoxycarbonyl with 1 to 5 carbon atoms in the alkoxy moiety, alkenoxycarbonyl with up to 5 carbon atoms in the alkenoxy moiety, alkylaminocarbonyl with 1 to 5 carbon atoms in the alkylamino moiety, phenyl, N-morpholino or dialkylamino with 1 to 6 carbon atoms per alkyl group; dialkylamino with 1 to 6 carbon atoms per alkyl group; phenyl or cyclohexyl.
$R^4$ is hydrogen or alkyl with 1 to 4 carbon atoms, which possesses insecticidal, acaricidal and fungicidal properties.

10 Claims, No Drawings

1-TRIORGANO-STANNYL-3-SUBSTITUTED-2,4-DIOXO-1,2,3,4-TETRAHYDRO-S-TRIAZINO-[1,2-a]-BENZIMIDAZOLES

The present invention relates to and has for its objects the provision of particular new 1-triorgano-stannyl-3-substituted-2,4-dioxo-1,2,3,4-tetrahydro-5-triazino-[1,2-2]-benzimidazoles, which possess insecticidal, acaricidal or fungicidal properties, active compositions in the form of mixtures of such compounds with solid and liquid dispersible carrier vehicles, and methods for producing such compounds and for using such compounds in a new way especially for combating pests, e.g. insects, acarids and fungi, with other and further objects becoming apparent from a study of the within specification and accompanying examples.

It is known from U.S. Pat. No. 3,546,240 and German Published Specifications DAS 2,143,252 and DOS 2,056,652 that a number of triorganyl-tin compounds exhibit a pesticidal action, as, for example, tricyclohexylstannyl-benzotriazole (Compound A), tricyclohexylstanyl-1,2,4-triazole (Compound B) and triphenylstannyl-imidazole (Compound C). However, the breadth and intensity of the insecticidal and acaricidal action of these compounds is not always satisfactory, especially if low amounts are used.

It is further known from German Published Specifications DOS 1,620,175, 1,745,784 and 1,806,123 that N-benzimidazol-2-ylcarbamic acid alkyl esters, and compounds which after application are converted to N-benzimadazol-2-ylcarbamic acid alkyl esters, exhibit a fungicidal action. These compounds however are inactive, or only slightly active, against Phycomycetes. Furthermore, in recent years, resistance against compounds of this type has developed in wide areas, so that their possible use is becoming greatly restricted.

The present invention provides 1-triorganostannyl-2,4-dioxo-1,2,3,4-tetrahydro-s-triazino[1,2-a]-benzimidazoles, substituted in the 3 -position, of the general formula

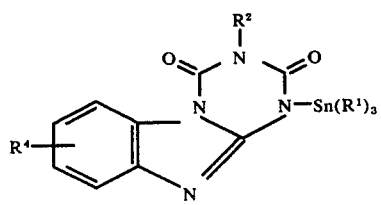

(I), in which $R^1$ is alkyl or cycloalkyl with 4 to 8 carbon atoms, or phenyl, and $R^2$ is alkyl with 1 to 18 carbon atoms optionally substituted by chlorine, CN, alkoxycarbonyl with 1 to 5 carbon atoms in the alkoxy moiety, alkenoxycarbonyl with up to 5 carbon atoms in the alkenoxy moiety, alkylaminocarbonyl with 1 to 5 carbon atoms in the alkylamino moiety, phenyl, N-morpholino or dialkylamino with 1 to 6 carbon atoms per alkyl group; is dialkylamino with 1 to 6 carbon atoms per alkyl group; phenyl or cyclohexyl.

$R^4$ is hydrogen or alkyl with 1 to 4 carbon atoms.

Preferably $R^1$ is butyl, cyclohexyl, n-octyl or phenyl, and $R^2$ is dialkylamino with 2 to 4 carbon atoms per alkyl group, cyclohexyl, phenyl, alkyl with 1 to 18 carbon atoms, or alkyl with 1 to 5, 10 or 11 carbon atoms substituted in the ω-position by CN, phenyl, alkoxycarbonyl with 2 to 4 carbon atoms in the alkenoxy moiety, N-morpholino or dialkylamino with 2 to 4 carbon atoms per alkyl group.

Particularly preferred compounds are those in which $R^1$ is butyl or cyclohexyl, and $R^2$ is butyl, methyl, tetradecyl,ω-cyanoalkyl or ω-alkoxycarbonylalkyl with 1 to 11 carbon atoms in the alkylene chain, N-morpholine-substituted propyl or dimethylamino, cyclohexyl, phenyl, ω-phenylethyl.

Surprisingly, the 3-substituted 1-triorgano-stannyl-2,4-dioxo-1,2,3,4-tetrahydro-s-triazino-[1,2-a]-benzimidazoles according to the invention exhibit a substantially greater insecticidal, acaricidal and fungicidal activity than the triorgano-tin-azoles known for the state of the art.

In addition, however, the compounds according to the invention also have a very good activity against those insects and mites which have already developed a high degree of resistance against phosphoric acid esters. The new compounds therefore meet an urgent requirement for better insecticidal compounds, which act in a different manner. Hence, the compounds according to the invention represent a valuable enrichment of the art.

The triazino-benzimidazole-tin compounds according to the present invention show a good fungicidal action. Their activity extends both to harmful fungi which are sensitive to N-benzimidazol-2-ylcarbamic acid alkyl esters and related compounds, and to resistant strains. Furthermore, they can be employed for combating fungi from the category of the Phycomycetes. Surprisingly, their fungicidal potency exceeds that of known triorganyl-tin-azoles.

If only because of the numerous possibilities in which they are superior when applied for biological purposes, the compounds according to the invention already represent a valuable enrichment of the art. In addition, however, the relatively low tin content of the active compounds according to the invention, resulting from the high molecular weight of the triazino-benzimidazole component, must be regarded as a technical advance, since tin is one of the elements in nature which is not available in great abundance, and which it is advisable to use sparingly.

The present invention also provides a process for the preparation of a compound of the formula (I) in which an alkali metal salt, alkaline earth metal salt or ammonium salt, which may be solvated, of a 2,4-dioxo-1,2,3,4-tetrahydro-s-triazino-[1,2-a]-benzimidazole, which is substituted in the 3-position, of the general formula

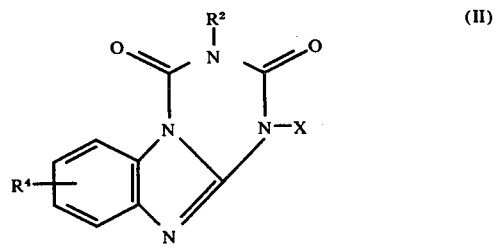

(II)

in which $R^2$ and $R^4$ have the aforementioned meanings,

X is one equivalent of an alkali metal ion or alkaline earth metal ion or represents $[HNR_3^3]^+$ or $[NR_4^3]^+$, preferably an alkali metal ion, and $R^3$ is an organic radical of a strongly basic ammonium ion, is reacted with a triorgano-tin halide of the general formula $$(R^1)_3Sn\text{-Hal} \qquad (III),$$

in which
$R^1$ has the abovementioned meaning and
Hal is chlorine, bromine or iodine.

If, for example, the sodium salt of 3-ω-cyanopentyl-2,4-dioxo-1,2,3,4-tetrahydro-s-triazino-[1,2-a]-benzimidazole and tributyltin chloride are used as starting materials, the course of the reaction can be represented by the following equation:

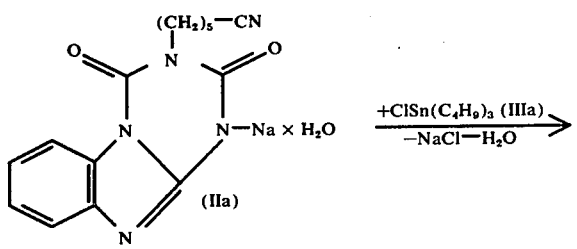

The 2,4-diodo-1,2,3,4-tetrahydro-s-triazino-[1,2-a]-benzimidazoles substituted in the 3-position are, in a number of cases, known from German Published Specification DOS 2,144,505. Those that are not described in the literature can be prepared in accordance with the processes described in the aforesaid specification. Alternatively, they can be obtained by cyclization of 1-(benzimidazol-2-yl)-ureas substituted in the 3-position, by subjecting these to the action of a diphenyl carbonate at temperatures between 140° and 220° C, preferably at 160° to 190° C, in accordance with the following equation:

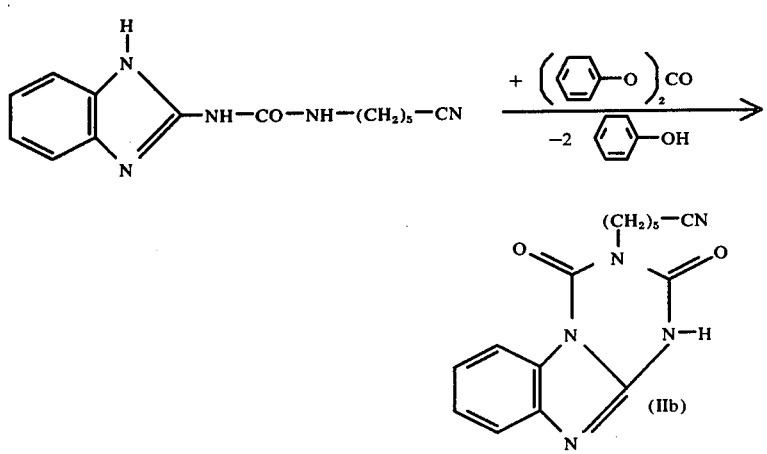

1-(Benzimidazol-2-yl)-ureas substituted in the 3-position are known from U.S. Pat. No. 3,399,212 and can be prepared in accordance with the process specified therein.

Examples of the starting materials of the formulas (II) or (III) to be reacted in accordance with the invention are: the sodium potassium, lithium, calcium, magnesium, strontium and barium salts, and trimethylammonium, triethylammonium, benzyldimethylammonium, cyclohexyldimethylammonium or dodecyltrimethylammonium salts of 3-ω-cyanoethyl-, 3-ω-cyanopentyl-, 3-ω-cyanopentyl-5-and 6-methyl-, 3-ω-cyanopentyl-5- and -6-butyl-, 3-ω-cyanopentyl-4- and -7-methyl-, 3-ω-cyanoundecyl-, 3-ω-chloroethyl-, 3-ω-chlorohexyl-, 3-methoxycarbonylmethyl-, 3-butoxycarbonylmethyl-, 3-ω-methoxycarbonyl-ethyl-, 3-ω-propoxycarbonyl-propyl-, 3-methoxycarbonylpentyl-, 3-ω-ethoxycarbonylpentyl-, 3-ω-methoxycarbonyldecyl-, 3-ω-methoxycarbonyl-undecyl-, 3-ω-allyloxycarbonyl-pentyl-, 3-ω-morpholinoethyl-, 3-ω-morpholinopropyl-, 3-ω-morpholinohexyl-, 3-dimethylaminoethyl-, 3-ω-dimethylaminopropyl-, 3-ω-diethylaminopropyl- and 3-dimethylamino-2,4-dioxo-1,2,3,4-tetrahydro-s-triazino-[1,2-a]-benzimidazoles, and tri-n-butyl-, tri-sec.-butyl-, tri-tert.-butyl-, tripentyl-, tri-n-octyl-, tricyclohexyl- or triphenyl-tin chlorides, bromides or iodides.

The compounds according to the invention are obtained when an alkali metal salt, alkaline earth metal salt or ammonium salt, which may be solvated, of a 3-substituted 2,4-dioxo-1,2,3,4-tetrahydro-s-triazino-[1,2-a]-benzimidazole is reacted with a triorgano-tin halide in an inert, preferably polar, solvent, such as dioxane, acetonitrile, benzonitrile or dimethylsulphoxide, or in a solvent mixture, at a temperature between 0° and 150° C, preferably at 40° to 60° C. The 1-triorganostannyl-2,4-dioxo-1,2,3,4-tetrahydro-s-triazino-[1,2-a]-benzimidazoles substituted in the 3-position are mostly more readily soluble than the 2,4-diodo-tetrahydro-s-triazino-benzimidazoles, substituted in the 3-position, which are employed, so that they can be separated, in solution in a suitable solvent, for example in chloroform or methylene chloride, from the starting compounds. After evaporating off the solvent, the product left in the residue must be purified by recrystallization, trituration or some other suitable measure. Some of the 1-triorganostannyl-2,4-diodo-tetrahydro-s-triazino-benzimidazoles substituted in the 3-position crystallize in more than one crystal form, and these forms differ in the IR spectra of potassium bromide pressed tablets but not in the IR spectra of their solutions.

The IR spectra of solutions of the compounds according to the invention in, for example, chloroform, differ clearly, in the region of 1,550 – 1,750 cm$^{-1}$, from the spectra of the 2,4-dioxo-tetrahydro-s-triazino-benzimidazoles substituted in the 3-position, for example in respect of the band sequence at 1,565, 1,585, 1,605 and 1,620 cm$^{-1}$. The melting points of the stannyl compounds are not always characteristic.

As already mentioned, the compounds according to the invention are insecticidally, acaricidally and fungicidally active. They can therefore be employed with advantage for combating sucking and biting insects as well as mites and phytopathogenic fungi. They are furthermore active, above all, against pests harmful to health and pests of stored products. In addition, their activity as dressings and cereal fungicides should be mentioned. Furthermore, at higher use concentrations they have a herbicidal effect when used for postemergence application. As a result of their microbistatic effect, they can furthermore be used for very diverse purposes in preservation, disinfection or antimicrobial finishing.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus meritimus*); thrips (*Thysanoptera*), such as *Hercinothrips femoralis*, and bugs, for example the beet bug (*Piesma quadrata*), the cotton bug (*Dysdercus intermedius*), the bed bug (*Cimex lectularius*), the assassin bug (*Rhodnius prolixus*) and Chagas' bug (*Triatoma infestans*), and, further, cicadas, such as *Euscelis bilobatus* and *Nephotettix bipunctatus*.

In the case of the biting insects, above all there should be mentioned butterfly and moth caterpillars (*Lipidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine oth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed gran beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the black current gall mite (*Eriophyes ribis*) and tarsonemids, for example the broad mite (*Hemitarsonems latus*) and the cyclamen mite (*Tarsonemus pallidus*); finally, ticks, such as the relapsing fever tick (*Ornithodorus moubata*).

When applied against pests harmful to health and pests of stored products, particulary flies and mosquitoes, the present compounds are also distinguished by an outstanding residual activity on wood and clay, as well as a good stability to alkali on limed substrates.

The active compounds according to the invention can be employed for combating harmful Archimycetes, Phycomycetes, Ascomycetes, Basidiomycetes and Fungi Imperfecti.

The active compounds according to the invention have both a protective action and a curative and systemic action. They can therefore be used, not only prophylactically, but also after an infection has occurred. It is also possible to deal with fungal diseases which develop in the system of the plant. The active compounds according to the invention may be employed for combating diseases, of a great variety of crop plants, which are caused by fungi and bacteria, such as species of Venturia (for example apple scab and pear scab), *Botrytis cinerea*, *Sclerotinia sclerotiorum*, species of Alternaria, species of Cercospora, *Mycospharella musicola*, *Phytophthora infestans*, *Plasmopara viticola*, species of Erysiphe and *Podosphaera leucotricha*.

The active compounds are also highly active, and of particular importance, when they are employed as seed dressings or soil treatment agents against phytopathogenic fungi which adhere to the seed or occur in the soil and cause shott diseases, root rots, tracheomycoses, and diseases of the stem, stalk, leaves, blossoms, fruit or seed in crop plants, such as *Tilletia caries*, *Helminthosphorium gramineum*, *Fusarium nivale*, *Fusarium*

*culmorum, Rhizoctonia solani, Phialophora cinerescens, Verticillium alboatrum, Fusarium dianthi, Fusarium cubense, Fusarium oxysporum, Fusarium solani, Sclerotinia sclerotiorum, Thielaviopsis basicola* and *Phyphophthora cactorum.*

It is also possible to combat bacteria which cause plant diseases, such as *Xanthomonas oryzae, Xanthomonas vesticatoria, Xanthomonas citri, Pseudomonas lachrymans, Pseudomonas morsphonorum, Pseudomonas solani* and species of *Erwinia.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/ or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and fungicides, or nematocides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over all compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of carrier vehicle assistant, e.g. a surface-agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In the treatment of seed, amounts of active compound of 0.1 to 10 g per kg of seed, preferably 0.5 to 5 g, are generally required. Amounts of active compound of 1 to 500 g per cubic meter of soil, preferably 10 to 200 g, are generally required for soil treatment.

Furthermore, the present invention contemplates methods of selectively killing, combating or controlling pests, e.g. insects, acarids and fungi, which comprises applying to at least one of correspondingly (a) such insects, (b) such acarids, (c) such fungi, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or fungicidally effective amount, of the particular active compound of the invention alone or together with a carrier vehicle as noted above. The instant formulations or compositions are applied in the usual manner, for instance by straying, atomizing, vaporizing, scattering, dusting, watering, squirting, sprinkling, pouring, fumigating, dressing, encrusting and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

LT$_{100}$ test for Diptera

Test insects:
  *Musca domestica*
Solvent:
  Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following Table 1:

Table 1

| Active compound | Active compound concentration of the solution in % | LT$_{100}$ |
|---|---|---|
| Known: | | |
| 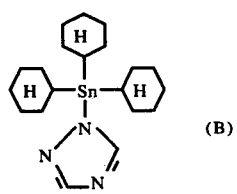 (B) | 0.2 | 8 hrs = 90% |
| 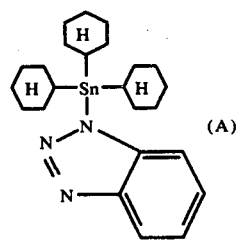 (A) | 0.2 | 8 hrs = 90% |
| According to the invention: | | |
| 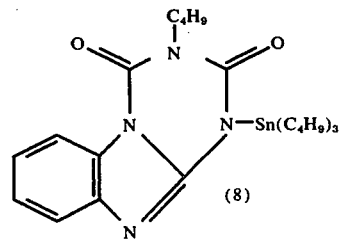 (8) | 0.2<br>0.02 | 130'<br>6 hrs |
| 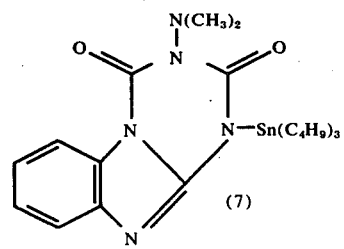 (7) | 0.2<br>0.02 | 170'<br>6 hrs = 90% |

Table 1-continued
LT$_{100}$ test for *Diptera* (*Musca domestica*)
| Active compound | Active compound concentration of the solution in % | LT$_{100}$ |
|---|---|---|
| 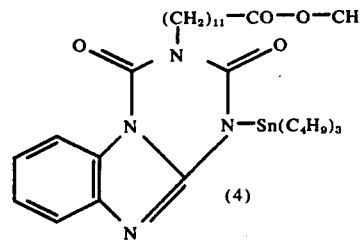 (4) | 0.2 | 120′ |
| 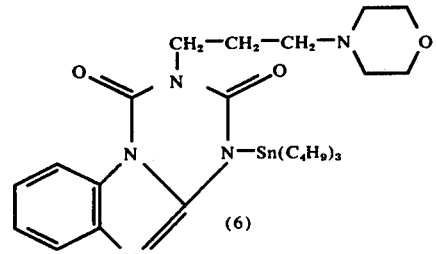 (6) | 0.2<br>0.02 | 70′<br>6 hrs = 80% |
| 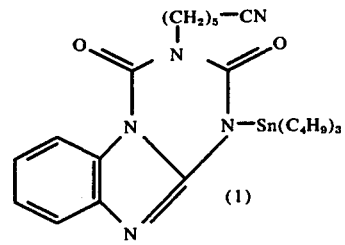 (1) | 0.2<br>0.02 | 50′<br>160′ |
| 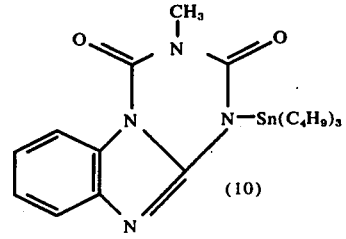 (10) | 0,2<br>0,02 | 65′<br>100′ |
| 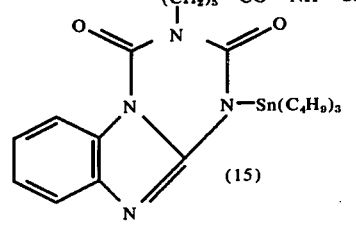 (15) | 0,2<br>0,02 | 110′<br>6$^h$ = 70 % |
| 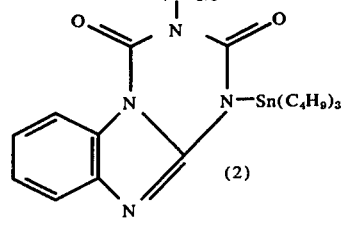 (2) | 0,2<br>0,02 | 50′<br>6$^h$ |

Table 1-continued
LT₁₀₀ test for *Diptera* (*Musca domestica*)
| Active compound | Active compound concentration of the solution in % | LT₁₀₀ |
|---|---|---|
| 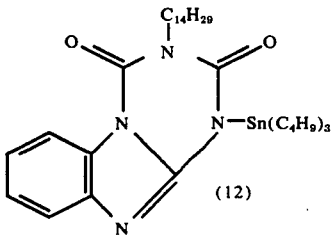 (12) | 0,2<br>0,02 | 80'<br>6ʰ = 90 % |
| 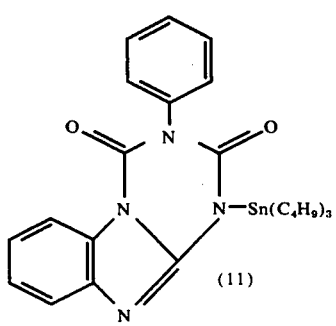 (11) | 0,2<br>0,02 | 45'<br>160' |
| 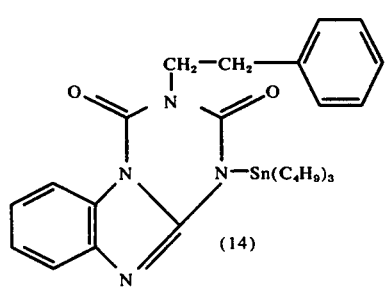 (14) | 0,2<br>0,02 | 65'<br>6ʰ/80 % |
| 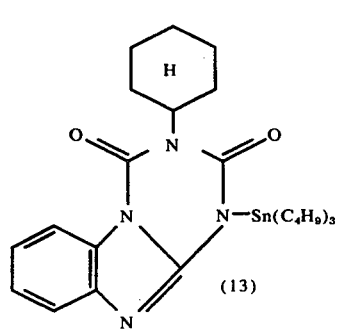 (13) | 0,2<br>0,02 | 80'<br>220' |
| 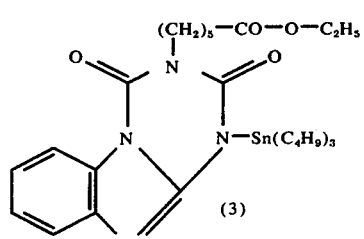 (3) | 0.2 | 85' |
EXAMPLE 2
LT₁₀₀ test for Diptera
Test insects:
*Aedes aegypti*
Solvent: Acetone
2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following Table 2:

Table 2

| | LT$_{100}$ test for *Diptera* (*Aedes aegypti*) | | |
|---|---|---|---|
| Active compound | | Active compound concentration of the solution in % | LT$_{100}$ |
| Known: | | | |
| 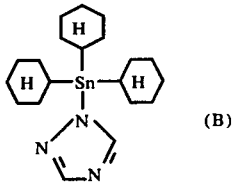 (B) | | 0.2 | 3 hrs = 0% |
| 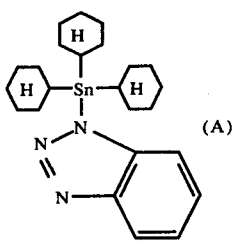 (A) | | 0.2 | 3 hrs = 0% |
| According to the invention: | | | |
| 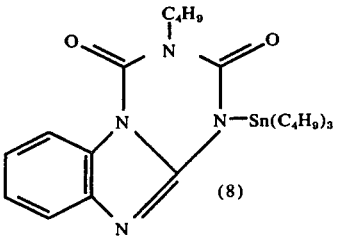 (8) | | 0.2<br>0.02 | 60'<br>60' |
| 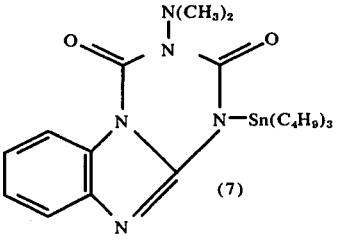 (7) | | 0.2<br>0.02 | 60'<br>3 hrs = 80% |
| 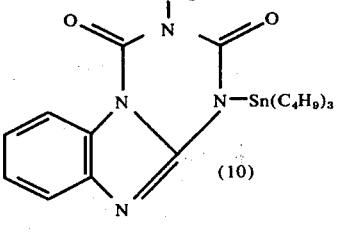 (10) | | 0,02 | 120' |

Table 2-continued
LT₁₀₀ test for Diptera (Aedes aegypti)
| Active compound | Active compound concentration of the solution in % | LT₁₀₀ |
|---|---|---|
| 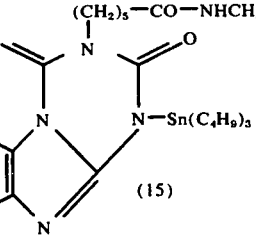 (15) | 0,02 | 120' |
| 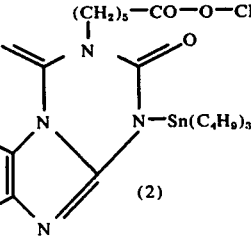 (2) | 0,02 | 120' |
| 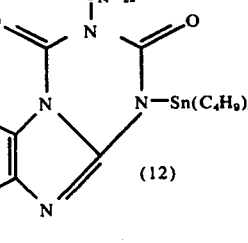 (12) | 0,02 | 180' |
| 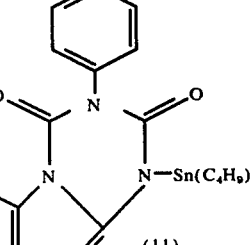 (11) | 0,02 | 160' |
| 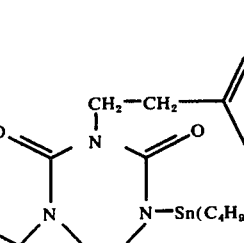 (14) | 0,02 | 60' |

Table 2-continued

| Active compound | LT$_{100}$ test for *Diptera* (*Aedes aegypti*) Active compound concentration of the solution in % | LT$_{100}$ |
|---|---|---|
| (13) | 0.02 | 180' |
| (4) | 0.2<br>0.02 | 60'<br>3 hrs = 50% |
| (6) | 0.2<br>0.02 | 60'<br>120' |
| (1) | 0.2<br>0.02 | 60'<br>60' |
| (3) | 0.2<br>0.02 | 60'<br>120' |

EXAMPLE 3

Tetranychus test (resistant)

Solvent:
3 parts by weight of dimethylformamide
Emulsifier:
1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 3:

Table 3

(Mites which harm plants)
*Tetranychus* test

| Active compound | Active compound concentration in % | Degree of destruction in % after 2 days |
|---|---|---|
| (C) (known) | 0.1 | 95 |
| | 0.01 | 0 |
| (7) | 0.1 | 100 |
| | 0.01 | 100 |
| (8) | 0.1 | 100 |
| | 0.01 | 100 |
| (1) | 0.1 | 100 |
| | 0.01 | 95 |
| (6) | 0.1 | 100 |
| | 0.01 | 98 |

Table 3-continued (Mites which harm plants)

*Tetranychus* test

| Active compound | Active compound concentration in % | Degree of destruction in % after 2 days |
|---|---|---|
| [structure with (CH$_2$)$_5$—CN (5), benzimidazole with N—Sn(C$_6$H$_{11}$)$_3$] | 0.1<br>0.01 | 100<br>100 |
| [structure with (CH$_2$)$_5$—CO—OCH$_3$, benzimidazole with N—Sn(C$_4$H$_9$)$_3$ (2)] | 0.1<br>0.01 | 100<br>100 |
| [structure with CH$_3$, benzimidazole with N—Sn(C$_4$H$_9$)$_3$ (10)] | 0.1<br>0.01 | 100<br>98 |
| [structure with phenyl, benzimidazole with N—Sn(C$_4$H$_9$)$_3$ (11)] | 0.1<br>0.01 | 100<br>98 |
| [structure with C$_{14}$H$_{29}$, benzimidazole with N—(C$_4$H$_9$)$_3$ (12)] | 0.1<br>0.01 | 100<br>100 |

Table 3-continued (Mites which harm plants)
Tetranychus test

| Active compound | Active compound concentration in % | Degree of destruction in % after 2 days |
|---|---|---|
| 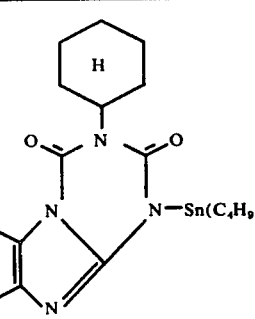 (13) | 0.1<br>0.01 | 100<br>98 |
| 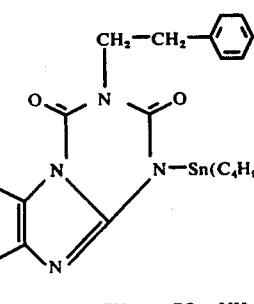 (14) | 0.1<br>0.01 | 100<br>99 |
| 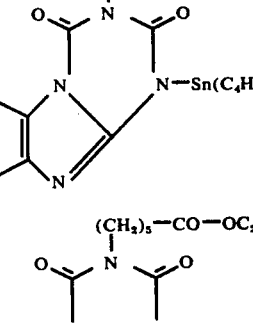 (15) | 0.1<br>0.01 | 100<br>100 |
| 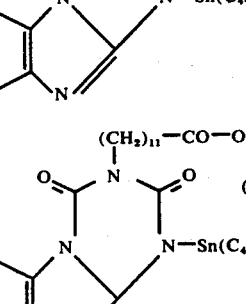 (3) | 0.1<br>0.01 | 100<br>98 |
| 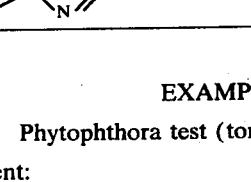 (4) | 0.1<br>0.01 | 100<br>100 |

EXAMPLE 4

Phytophthora test (tomatoes)/protective

Solvent:
    4.7 parts by weight of acetone
Emulsifier:
    0.3 part by weight of alkylaryl polyglycol ether
Water:
    95.0 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to percent infection: 0% means no infection; 100% means that the plants were totally infected.

The active compound, the concentrations of the active compound and the results can be seen from the following Table 4:

The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C and at a relative atmospheric humidity of 70%. They were then inoculated with an aqueous conidium suspension of the apple scab causative organism (*Fusicladium dendriticum Fuckel*) and incubated for 18 hours in a humidity chamber at 18°–20° C and at a relative atmospheric humidity of 100%.

Table 4

*Phytophthora* test (tomatoes)/protective

| Active compound | Infection in % at an active compound concentration of 0.0062%  0.00156% |
|---|---|
| known: (B) | 100 |
| According to the invention: (1) | 11 |

EXAMPLE 5

Fusicladium test (apple scab) /Protective

Solvent:
4.7 parts by weight of acetone
Emulsifier: 0.3 part by weight of alkylaryl polyglycol ether
Water:
95.0 parts by weight The plants were then brought into a greenhouse for 14 days.

15 days after inoculation, the infection of the seedlings were determined as a percentage of the untreated but also inoculated control plants.

0% means no infection; 100% means that the infection was exactly as great as in the case of the control plants.

The active compounds, the concentrations of the active compounds and the results can be seen from the following Table 5:

Table 5

*Fusicladium* test (apple)/protective

| Active compound | Infection in % at an active compound concentration of 0.0062%  0.0025% |
|---|---|
| Known | |

Table 5-continued

*Fusicladium* test
(apple)/protective

| Active compound | Infection in % at an active compound concentration of 0.0062%  0.0025% |
|---|---|
| (B) tricyclohexyltin-triazole structure | 72 |

According to the invention:

| Compound (1): benzimidazole with N−(CH₂)₅−CN and N−Sn(C₄H₉)₃ | 1 |
| Compound (3): benzimidazole with N−(CH₂)₅−CO−O−C₂H₅ and N−Sn(C₄H₉)₃ | 57 |
| Compound (8): benzimidazole with N−C₄H₉ and N−Sn(C₄H₉)₃ | 0 |
| Compound (4): benzimidazole with N−(CH₂)₁₁−CO−O−CH₃ and N−Sn(C₄H₉)₃ | 22 |
| Compound (2): benzimidazole with N−(CH₂)₅−CO−O−CH₃ and N−Sn(C₄H₉)₃ | 0 |

4,026,934

Table 5-continued

*Fusicladium* test (apple)/protective

| Active compound | Infection in % at an active compound concentration of 0.0062% | 0.0025% |
|---|---|---|
| 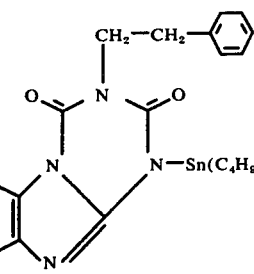 (14) | 10 | |
| 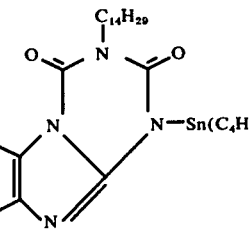 (12) | 7 | |
| 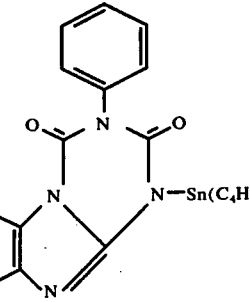 (11) | 10 | |
| 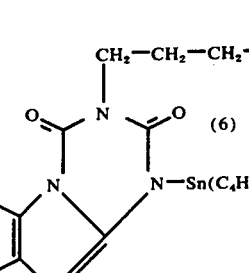 (6) | 32 | |

EXAMPLE 6

Mycelium growth test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of $Na_2HPO_4$, and
  0.3 part by weight of $Ca(NO_3)_2$, per 1,000 ccs. of water Composition of the solvent mixture:
  0.19 part by weight of dimethylformamide or acetone
  0.01 part by weight of emulsifier (alkylaryl polyglycol ether)
  1.80 parts by weight of water Ratio of solvent mixture to nutrient medium:
  2 parts by weight of solvent mixture
  100 parts by weight of agar nutrient medium The amount of active compound required for the desired active compound concentration in the nutrient medium was mixed with the stated amount of solvent. The concentrate was thoroughly mixed, in the stated proportion, with the liquid nutrient medium (which had been cooled to 42° C) and was then poured into Petri dishes of 9 cm diameter. Control plates to which the preparation had not been added were also set up.

When the nutrient medium had cooled and solidified, the plates were inoculated with the species of fungi stated in the following table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values are used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following Table 6:

Table 6

| Active compounds | Active compound concentration in ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinera | Verticillium alboatrum | Pyricularia oryzae | Phialophora cinerescens | Helminthosphorium gramineum | Mycosphaerella musicola | Phytophthora cactorum | Pellicularia sasakii | Xanthomonas oryzae | Pseudomonas lachrymans | Venturia inaequalis |
|---|---|---|---|---|---|---|---|---|---|---|---|---|---|---|---|---|---|---|---|
| (C) (known) [Sn(phenyl)₃-triazole] | 10 | — | — | — | 7 | — | — | 3 | — | 5 | 1 | 9 | — | 1 | — | 9 | 9 | — | — |
| (B) (known) [Sn(cyclohexyl)₃-triazole] | 10 | — | — | — | 1 | — | — | 5 | — | 5 | — | 5 | — | 1 | — | 7 | 7 | — | — |
| (8) C₄H₉ ... Sn(C₄H₉)₃ | 10 | 2 | 1 | 1 | 1 | 1 | 1 | 1 | 1 | 1 | 1 | 2 | 1 | 1 | 1 | 1 | 3 | 2 | — |
| (4) (CH₂)₁₁—CO—O—CH₃ ... N—Sn(C₄H₉)₃ | 10 | 1 | 1 | 1 | 1 | 1 | 1 | 1 | 1 | 1 | 1 | 1 | 1 | 1 | 1 | 1 | — | 2 | — |

Table 6-continued

Mycelium growth test

| Active compounds | Active compound concentration in ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinera | Verticillium alboatrum | Pyricularia oryzae | Phialophora cinerescens | Helminthosporium gramineum | Mycosphaerella musicola | Phytophthora cactorum | Pellicularia sasakii | Xanthomonas oryzae | Pseudomonas lachrymans | Venturia inaequalis |
|---|---|---|---|---|---|---|---|---|---|---|---|---|---|---|---|---|---|---|---|
| (6) CH₂—CH₂—N(morpholine), CH₂ on N; ring N—Sn(C₄H₉)₃ | 10 | 1 | 1 | 2 | 1 | 1 | 1 | 1 | 1 | 1 | 1 | 1 | 1 | 1 | 1 | 1 | 1 | 1 | — |
| (1) (CH₂)₅—CN; N—Sn(C₄H₉)₃ | 10 | 1 | 1 | 1 | 1 | 1 | 1 | 1 | 1 | 1 | 1 | 5 | 1 | 1 | 1 | 1 | 1 | 1 | — |
| (3) (CH₂)₅—CO—O—C₂H₅; N—Sn(C₄H₉)₃ | 10 | 1 | 1 | 1 | 1 | 1 | 1 | 1 | 1 | 1 | 1 | 1 | 1 | 1 | 2 | 1 | 3 | 2 | — |
| (7) N(CH₃)₂; N—Sn(C₄H₉)₃ | 10 | 2 | 1 | 2 | 1 | 1 | 1 | 1 | 1 | 1 | 1 | 2 | 1 | 1 | 2 | 1 | 3 | 1 | — |

Table 6-continued

| | | Mycelium growth test | | | | | | | | | | | | | | Fungi and 2 bacteria | |
|---|---|---|---|---|---|---|---|---|---|---|---|---|---|---|---|---|---|
| Active compounds | Active compound concentration in ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinera | Verticillium alboatrum | Pyricularia oryzae | Phialophora cinerescens | Helminthosphorium gramineum | Mycosphaerella musicola | Phytophthora cactorum | Pellicularia sasakii | Xanthomonas oryzae | Pseudomonas lachrymans | Venturia inaequalis |

(Structures shown for compounds (2), (10), (11), (12), all containing N—Sn(C₄H₉)₃ groups attached to fused benzimidazole-triazine-dione systems, with substituents (CH₂)₅—CO—O—CH₃, CH₃, C₆H₅ (phenyl), and C₁₄H₂₉ respectively.)

Compound (2): concentration 10 ppm — all entries "—"
Compound (10): all entries "—"
Compound (11): all entries "—"
Compound (12): concentration 10 ppm — all entries "—"

Table 6-continued

| Active compounds | Active compound concentration in ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinera | Verticillium alboatrum | Pyricularia oryzae | Phialophora cinerescens | Helminthosporium gramineum | Mycosphaerella musicola | Phytophthora cactorum | Pellicularia sasakii | Xanthomonas oryzae | Pseudomonas lachrymans | Venturia inaequalis |
|---|---|---|---|---|---|---|---|---|---|---|---|---|---|---|---|---|---|---|---|
| 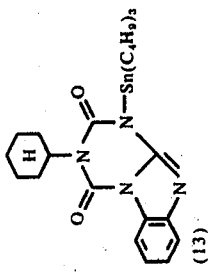 (13) | | — | — | — | — | — | — | — | — | — | — | — | — | — | — | — | — | — | — |
| 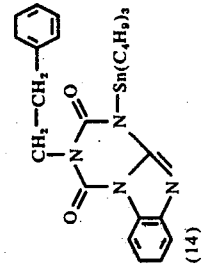 (14) | | — | — | — | — | — | — | — | — | — | — | — | — | — | — | — | — | — | — |
| 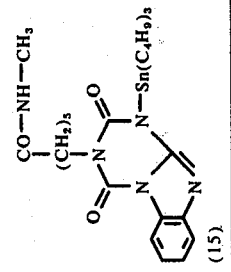 (15) | 10 | — | — | — | — | — | — | — | — | — | — | — | — | — | — | — | — | — | — |

EXAMPLE 7

Test of the cross-resistance to MCB (methyl 2-benzimidazole carbamate) in the plate test with Colletotrichum coffeanum In the experiment, strains of *Colletotrichum coffeanum* which are sensitive or resistant to MBC or MBC-forming formulations were used.

Description of the method:

The nutrient medium used was potato-dextrose agar of the following composition:

potato infusion: 4 g
D(+) glucose: 20 g
peptone: 10 g
malt: 5 g
agar-agar: 20 g per 1,000 ml of water.

400 cm$^3$ of fluid potato-dextrose-agar cooled to 45° C were thoroughly mixed with 6 cm$^3$ of a spore suspension of *Colletotrichum coffeanum* at a density of 1,000,000 spores/ml and the mixture was poured, in amounts of 20 cm$^3$ of agar, into Petri dishes of 9 cm diameter.

A formulation with an active compound concentration of 10,000 ppm was prepared from the comparison formulations to be tested and from the compounds according to the invention. A mixture of 47% of acetone, 47% of dimethylformamide and 6% of emulsifier (alkylaryl polyglycol ether) was used to dissolve the formulation. From this, formulations with concentrations of 5,000, 1,000, 100, 50, 25 and 10 ppm were prepared by dilution with water. Filtertips of 10 mm diameter from Messrs. Schleicher & Schull were dipped into these formulations and groups of 4 plates were set up with 4 different concentrations per agar dish.

It can be seen from the following table that on the plates on which plates with a concentration of 10,000 to 100 ppm of MBC or Cypendazol were set up, no mycelium growth resulted in the case of the sensitive strain. With the same formulations and the same strain of fungus, measurable inhibition zones were detectable at 10 ppm. In the case of the resistant strains, no action was detectable with MBC at up to 10,000 ppm. Cypendazol only showed a small inhibition zone at as much as 5,000 ppm.

In comparison to these results, the compounds according to the invention were able to inhibit both the sensitive and the resistant strain to almost the same degree at the concentrations tested.

This result shows clearly that the two compounds according to the invention tested here have no cross-resistance with MBC or MBC-forming formulations.

The active compounds, the active compounds concentrations and the results can be seen from the following Table 7:

Table 7
Test of cross-resistance to BCM (benzimidazole-methylcarbamate) in the plate test using *Colletotrichum coffeanum*
| | | BCM- and Cypendazol-resistant strain | | | | | | | | BCM- and Cypendazol-sensitive strain | | | | | | | |
|---|---|---|---|---|---|---|---|---|---|---|---|---|---|---|---|---|---|
| | | Plate 1 | | | Plate 2 | | | | | Plate 1 | | | | Plate 2 | | | |
| Structure | Concentration in ppm = | 10,000 | 5,000 | 1,000 | 100 | 100 | 50 | 25 | 10 | 10,000 | 5,000 | 1,000 | 100 | 100 | 50 | 25 | 10 |
| (MBC) | | 0 | 0 | 0 | 0 | 0 | 0 | 0 | 0 | x̄ | x̄ | x̄ | x̄ | x̄ | x̄ | 11 | 10 |
| (Cypendazole) | | 10 | 8 | 0 | 0 | 0 | 0 | 0 | 0 | x̄ | x̄ | x̄ | x̄ | x̄ | 12 | 9 | 7 |
| (7) | | 15 | 12 | 10 | 4 | 5 | 3 | 2 | 1 | 13 | 10 | 9 | 4 | 5 | 5 | 2 | 0 |
| (8) | | x̄ | 14 | 11 | 7 | 8 | 6 | 5 | 4 | 13 | 10 | 9 | 5 | 5 | 4 | 4 | 3 |
The inhibition zone is measured in mm  x̄ = total inhibition
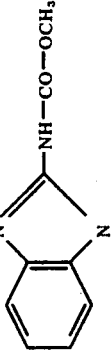
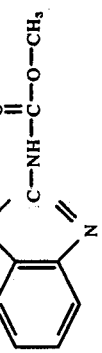
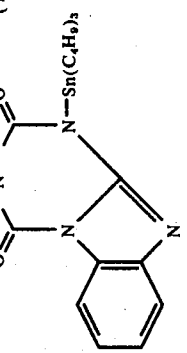
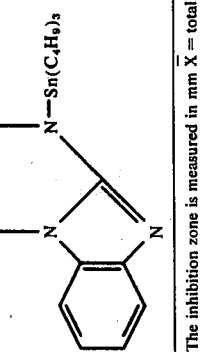

The process of the present invention is illustrated by the following preparative Examples.

EXAMPLE 8 a. 3-ω-Cyanopentyl-2,4-dioxo-1,2,3,4-tetrahydro-s-triazino-[1,2-a]-benzimidazole, melting point 258° C, was synthesized by the action of diphenyl carbonate on 1-(benzimidazol-2-yl)-3-(ω-cyanopentyl)-urea, melting point >330° C. The urea derivative was prepared by rearrangement of 1-(ω-cyanopentylcarbamoyl)-2-amino-benzimidazole, known from U.S. Pat. No. 3,673,210, by the process according to U.S. Pat. No. 3,399,212.

(b)
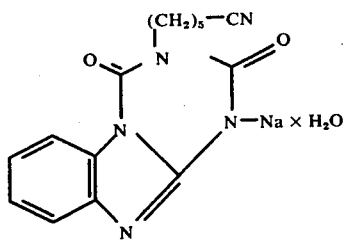

286 g of 3-ω-cyanopentyl-2,4-dioxo-1,2,3,4-tetrahydro-s-triazino-[1,2-a]-benzimidazole and 39 g of sodium hydroxide were boiled for 4 hours in 4 liters of alcohol. The solution was filtered hot and concentrated to a volume of 1 liter. The sodium 3-ω-cyanopentyl-2,4-dioxo-1,2,3,4-tetrahydro-s-triazino-[1,2-a]-benzimidazole monohydrate crystallized out and was separated off. A second crystal fraction was obtained by concentrating the mother liquor.

Yield: 288 g after drying at 100° C/0.1 mm Hg. IR(KBr) bands at 1,560, 1,595, 1,620, 1,720 and 2,240 cm$^{-1}$.

(c)
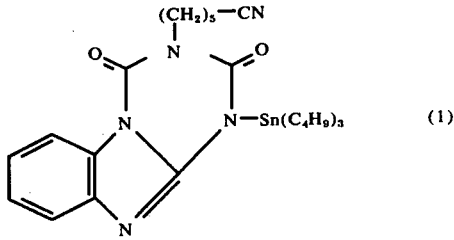

60 g of sodium 3-ω-cyanopentyl-2,4-dioxo-1,2,3,4-tetrahydro-s-triazino-[1,2-a]-benzimidazole monohydrate, 500 ml of acetonitrile and 65 g of tributyl-tin chloride were stirred for 22 hours. The precipitate was filtered off, the reaction mixture was taken up in 4 liters of chloroform and the whole was filtered. The solution was clarified with bone charcoal and then evaporated, and the resulting residue was triturated with dibutyl ether.

Yield: 74.3 g of 1-tributyl-stannyl-3-ω-cyanopentyl-2,4-dioxo-1,2,3,4-tetrahydro-s-triazino-[1,2-a]-benzimidazole. Melting point: 110.5° C; C found 55.5%, C calculated 55.3%.

EXAMPLE 9 a. The starting material 3-ω-methoxycarbonylpentyl-2,4-dioxo-1,2,3,4-tetrahydro-s-triazino-[1,2-a]-benzimidazole of melting point 221° C was prepared by reaction of 1-(benzimidazol-2-yl)-3-(ω-methoxycarbonylpentyl)-urea, melting point > 330° C, with diphenyl carbonate at 160° C.

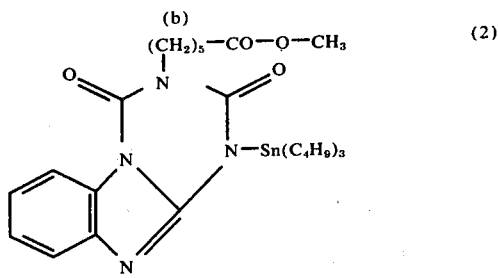

3.4 g of sodium hydroxide, dissolved in 20 ml of water, were added, while cooling, to 28.2 g of 3-ω-methoxycarbonylpentyl-2,4-dioxo-1,2,3,4-tetrahydro-s-triazino-[1,2-a]-benzimidazole and 400 g of dimethylsulphoxide. About 126 g of solvent were distilled off at 13 mm Hg. 27.7 g of tributyl-tin chloride were added to the residue and the reaction mixture was kept at 45° C for 11 hours. 1 liter of chloroform was added, the reaction mixture was washed repeatedly with water and the unconverted methoxycarbonylpentyl-dioxo-tetrahydro-triazino-benzimidazole was filtered off. The chloroform solution was evaporated in vacuo. The residue was taken up in 500 ml of toluene and the solution was clarified and evaporated. The residue was triturated with methylcyclohexane, and dried.

Yield: 25 g of 1-tri-butyl-stannyl-3-ω-methoxycarbonylpentyl-2,4-dioxo-1,2,3,4-tetrahydro-s-triazino[1,2-a]-benzimidazole of melting point 106° C.

The following compounds were prepared analogously:

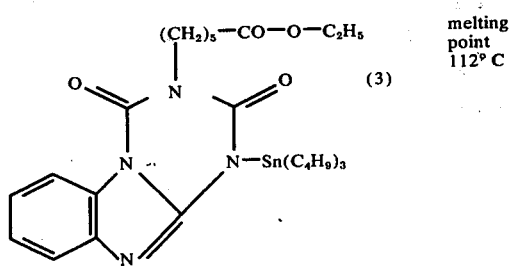
melting point 112° C

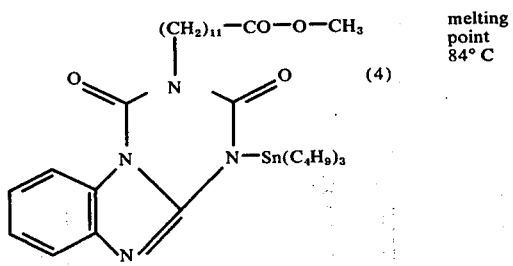
melting point 84° C

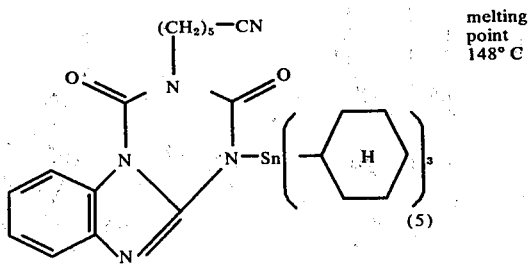
melting point 148° C

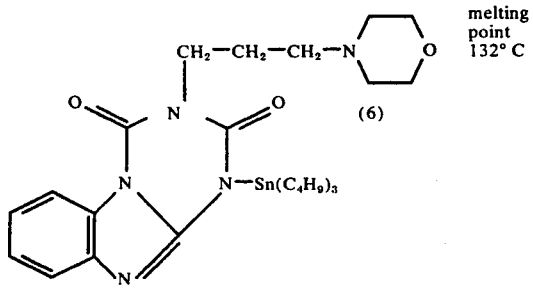

(6) melting point 132° C

EXAMPLE 10 a. Preparation of the intermediate 1,1-dimethyl-4-(benzimidazol-2-yl)-semicarbazide was effected as follows:

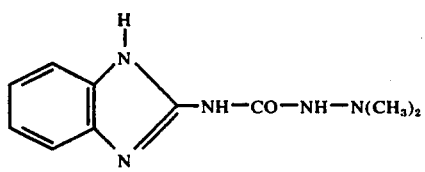

A mixture of 3 moles of benzimidazol-2-yl-carbamic acid phenyl ester and 2,100 g of phenol was stirred with 240 g $N^1,N^1$-dimethylhydrazine for 7 hours at 70° C. The reaction mixture was filtered and concentrated in vacuo. 1.6 liters of acetonitrile was added to the residue. The mixture was cooled to 0° C. The crystals were separated off and washed with acetonitrile and with water to which a small amount of a surface-active agent had been added. They were then dried at 100° C/3 mm Hg.

Yield: 573 g of 1,1-dimethyl-4-(benzimidazol-2-yl)-semicarbazide. Melting point >330° C. The IR spectrum of KBr pressed tablets showed, inter alia, strong bands at 1,512 and 1,575 $cm^{-1}$.

(b)

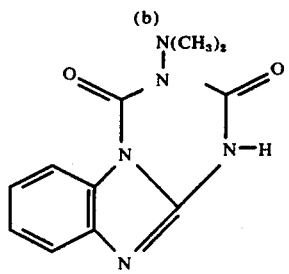

394 g of 1,1-dimethyl-4-(benzimidazol-2-yl)-semicarbazide, 428 g of diphenyl carbonate, 650 g of benzonitrile, and 2,200 g of phenol were kept at 160° C for 24 hours. The mixture of benzonitrile and phenol was largely distilled off under 13 mm Hg. 900 ml of acetonitrile were added to the residue. The crystals were separate off, washed with acetonitrile and water and finally dried at 100° C/3 mm Hg.

Yield: 360 g of crude 3-dimethylamino-2,4-dioxo-1,2,3,4-tetrahydro-s-triazino-[1,2-a]-benzimidazole.

For purification, the compound was dissolved in a boiling mixture of 5 liters of water, 3 liters of alcohol and 88 g of potassium hydroxide. The solution was filtered cold. The filtrate was adjusted to pH 4. The precipitate was separated off and washed free from salt.

Yield: 308 g of purified compound. Melting point >330° C. Calculated: N 28.56%. Found: N 28.5%.

The IR spectrum in KBr showed strong carbonyl bands at 1,620 to 1,640 $cm^{-1}$, 1,695 - 1,705 $cm^{-1}$ and 1,745 $cm^{-1}$.

By the process of Example 8(c) 3-dimethylamine-2,4-dioxo-1,2,3,4-tetrahydro-s-triazino-1,2-a]-benzimidazole was reacted with tributyl-tin chloride to produce 1-tributylstannyl-3-dimethylamino-2,4-dioxo-1,2,3,4-tetrahydro-s-triazino-[1,2-a]-benzimidazole.

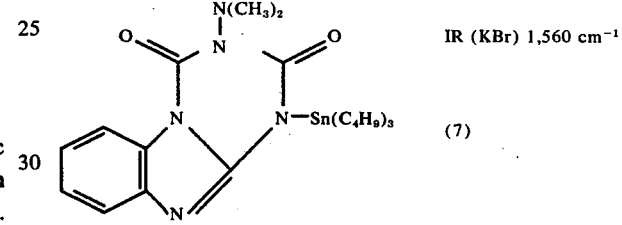

IR (KBr) 1,560 $cm^{-1}$ (7)

The following compounds were prepared analogously to Examples 8 to 10:

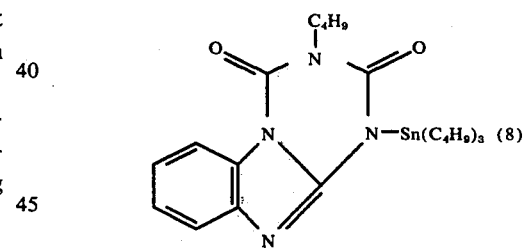

(8)

Melting point 132° C, with decomposition. IR (CHCl₃) 1,568, 1,585, 1,605, 1,622, 1,660 and 1,730 $cm^{-1}$.

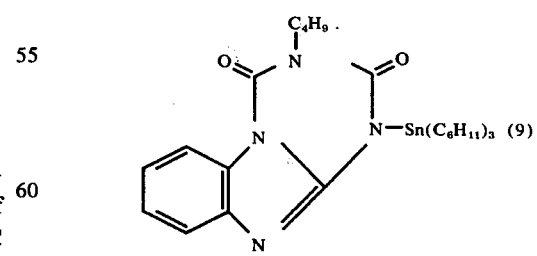

(9)

Crystallized once from toluene and once from acetone.

Melting point 100° C, with decomposition. IR(CHCl₃) 1,562, 1,580, 1,602, 1,618, 1,665 and 1,725 $cm^{-1}$.

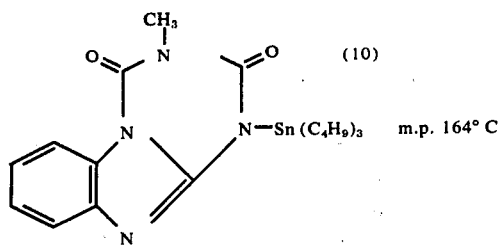

m.p. 164° C (10)

The starting material 3-methyl-2,4-dioxo-1,2,3,4-tetrahydro-s-triazino-[1,2-a]-benzimidazole is known from German Published Specification DOS 2,144,505

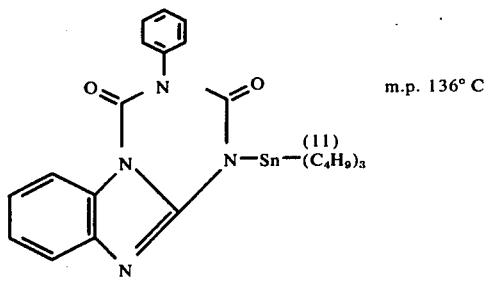

m.p. 136° C (11)

The starting material 3-phenyl-2,4-dioxo-1,2,3,4-tetrahydro-s-triazino-[1,2-a]-benzimidazole is known from German Published Specification DOS 2,144,505.

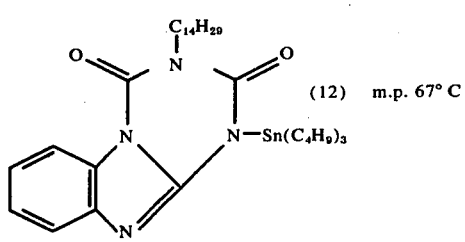

(12) m.p. 67° C

The starting material 3-tetradecyl-2,4-dioxo-1,2,3,4-tetrahydro-s-triazino-[1,2-a]-benzimidazol (m.p. 193° C) is obtained by reacting 1-(benzimidazole-2-yl)-3-tetradecylurea and diphenylcarbonate. 1-(benzimidazole-2-yl)-3-tetradecylurea is formed by the reaction of 2-aminobenzimidazole and tetradecylisocyanate in xylene at 120° C.

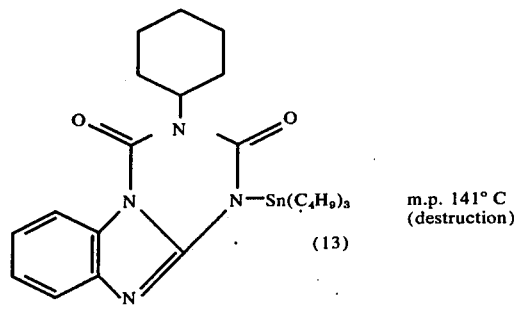

m.p. 141° C (destruction) (13)

The starting material 3-cyclohexyl-2,4-dioxo-1,2,3,4-tetrahydro-s-triazino[1,2-a]-benzimidazole (m.p. 335° C) is obtained from 1-(benzimidazole-2-yl)-3-cyclohexylurea and diphenylcarbonate. 1-(benzimidazole-2-yl)-3-cyclohexylurea is obtained from 2-aminobenzimidazole and cyclohexylisocyanate at about 120° C in xylene.

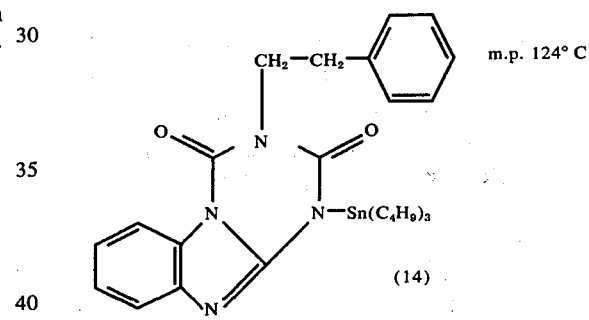

m.p. 124° C (14)

The starting material 3-(2-phenylethyl)-2,4-dioxo-1,2,3,4-tetrahydro-s-triazino-[1,2-a]-benzimidazole (m.p. 298° C) is produced from diphenylcarbobate and 1-(benzimidazole-2-yl)-3-(2-phenylethyl)-urea. The latter is produced from N-benzimidazole-2-yl-carbamic acid phenyl ester and 2-phenylethylamine.

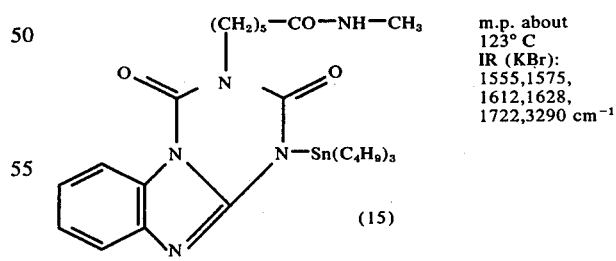

m.p. about 123° C
IR (KBr): 1555,1575, 1612,1628, 1722,3290 cm$^{-1}$ (15)

The starting material 3-(ω-methylamino-carbonylpentyl)-2,4-dioxo-1,2,3,4-tetrahydro-s-triazino-[1,2-a]-benzimidazole (m.p. 268° C destr.) is formed by boiling 3-(ω-methoxycarbonylpentyl)-2,4-dioxo-1,2,3,4-tetrahydro-s-triazino-[1,2-a]-benzimidazole (m.p. 221° C) in a mixture of butanol and water with methylamine.

It will be appreciated that the instant specification and examples are set forth by way of illustration and not limitation, and that various modifications and changes may be made without departing from the spirit and scope of the present invention.

What we claim is:

1. A 1-triorgano-stannyl-3-substituted-2,4-dioxo-1,2,3,4-tetrahydro-s-triazino-[1,2-a]-benzimidazole of the formula

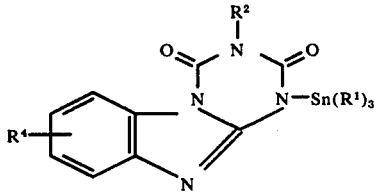

in which $R^1$ is alkyl or cycloalkyl with 4 to 8 carbon atoms, or phenyl, and $R^2$ is alkyl with 1 to 1 carbon atoms optionally substituted by chlorine, CN, alkoxycarbonyl with 1 to 5 carbon atoms in the alkoxy moiety, alkenoxycarbonyl with up to 5 carbon atoms in the alkenoxy moiety, phenyl, alkylaminocarbonyl with 1 to 5 carbon atoms in the alkylamino moiety, N-morpholino or dialkylamino with 1 to 6 carbon atoms per alkyl group; dialkylamino with 1 to 6 carbon atoms per alkyl group; cyclohexyl or phenyl, $R^4$ is hydrogen or alkyl with 1 to 4 carbon atoms.

2. A compound according to claim 1, in which $R^1$ is butyl, cyclohexyl, n-octyl or phenyl, $R^2$ is dialkylamino with 2 to 4 carbon atoms per alkyl group, cyclohexyl, phenyl, or alkyl with 1 to 5, 10 or 11 carbon atoms optionally substituted in the ω-position by CN, phenyl, alkoxycarbonyl with 1 to 4 carbon atoms in the alkoxy moiety, alkenoxycarbonyl with 2 to 4 carbon atoms in the alkenoxy moiety, N-morpholino or dialkylamino with 2 to 4 carbon atoms per alkyl group.

3. The compound according to claim 1 wherein such compound is 1-tributyl-stannyl-3-w-cyanopentyl-2,4-dioxo-1,2,3,4-tetra-hydro-s-triazino-[1,2-a]-benzimidazole of the formula

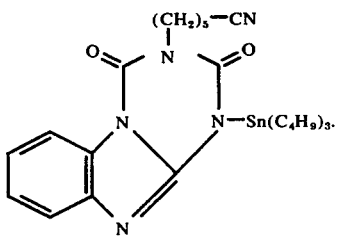

4. The compound according to claim 1 wherein such compound is 1-tributyl-stannyl-3-ω-butyl-2,4-dioxo-1,2,3,4-tetra-hydro-s-triazino-[1,2-a]-benzimidazole of the formula

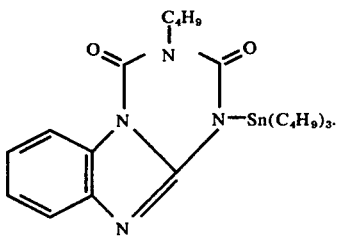

5. The compound according to claim 1 wherein such compound is 1-tributyl-stannyl-3-methyl-2,4-dioxo-1,2,3,4-tetra-hydro-s-triazino-[1,2-a]-benzimidazole of the formula

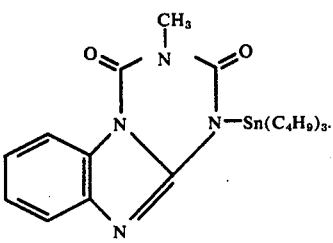

6. The compound according to claim 1 wherein such compound is 1-tributyl-stannyl-β-phenyl-2,4-dioxo-1,2,3,4-tetra-hydro-s-triazino-[1,2-a]-benzimidazole of the formula

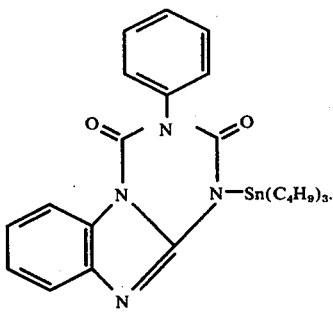

7. The compound according to claim 1 wherein such compound is 1-tributyl-stannyl-3-cyclohexyl-2,4-dioxo-1,2,3,4-tetra-hydro-s-triazino-[1,2-a]-benzimidazole of the formula

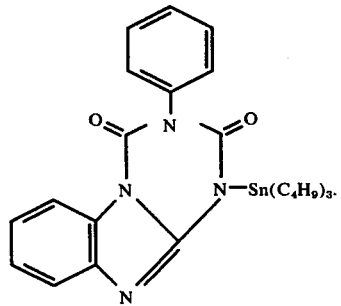

8. An insecticidal, acaricidal or fungicidal composition containing as active ingredient an insecticidally, acaricidally or fungicidally effective amount of a compound according to claim 1 in admixture with a diluent.

9. A method of combating insects, acarids or fungi which comprises applying to the insects, acarids or fungi or to a habitat thereof an insecticidally, acaricidally or fungicidally effective amount of a compound according to claim 1.

10. The method according to claim 9 in which said compound is 1-tributyl-stannyl-3-ω-cyanopentyl-2,4-dioxo-1,2,3,4-tetra-hydro-s-triazino-[1,2-a]-benzimidazole, 1-tributyl-stannyl-3-n-butyl-2,4-dioxo-1,2,3,4-tetra-hydro-s-triazino-[1,2-a]-benzimidazole, 1-tributyl-stannyl-3-methyl-2,4-dioxo-1,2,3,4-tetra-hydro-s-triazino-[1,2-a]-benzimidazole, 1-tributyl-stannyl-3-phenyl-2,4-dioxo-1,2,3,4-tetra-hydro-s-triazino-[1,2-a]-benzimidazole or 1-tributyl-stannyl-3-cyclohexyl-2,4-dioxo-1,2,3,4-tetra-hydro-s-triazino-[1,2-a]-benzimidazole.

* * * * *

UNITED STATES PATENT AND TRADEMARK OFFICE
CERTIFICATE OF CORRECTION

PATENT NO. : 4,026,934
DATED : May 31, 1977
INVENTOR(S) : Werner Daum, et al.

It is certified that error appears in the above-identified patent and that said Letters Patent are hereby corrected as shown below:

| | |
|---|---|
| Col. 1, line 45 | delete "$R^4$" in formula |
| Col. 2, line 13 | cancel "for" and substitute -- from -- |
| Col. 2, line 65 | cancel "aforementioned" and substitute -- abovementioned -- |
| Col. 3, line 35 | cancel "diodo-" and substitute -- dioxo- -- |
| Col. 4, line 5 | after "sodium" insert -- , -- |
| Col. 4, line 37 | cancel "diodo-" and substitute -- dioxo- -- |
| Col. 4, line 45 | cancel "diodo-" and substitute -- dioxo- -- |
| Col. 5, line 37 | cancel "meritimus" and substitute -- maritimus -- |
| Col. 5, line 46 | cancel "Lipidoptera" and substitute -- Lepidoptera -- |
| Col. 5, line 55 | cancel "oth" and substitute -- moth -- |

UNITED STATES PATENT AND TRADEMARK OFFICE
CERTIFICATE OF CORRECTION

PATENT NO. : 4,026,934
DATED : May 31, 1977
INVENTOR(S) : Werner Daum, et al.

It is certified that error appears in the above-identified patent and that said Letters Patent are hereby corrected as shown below:

| | |
|---|---|
| Col. 5, line 56 | cancel "Kuhniella" and substitute -- Kühniella -- |
| Col. 6, line 3 | cancel "gran" and substitute -- grain -- |
| Col. 6, line 25 | cancel "Aedes" and substitute -- Aëdes -- |
| Col. 6, line 34 | cancel "Hemitarsonems" and substitute -- Hemitarsonemus -- |
| Col. 6, line 38 | cancel "particulary" and substitute -- particularly -- |
| Col. 6, line 62 | after "particular" insert -- practical -- |
| Col. 8, line 25 | after "surface" insert -- active -- |
| Col. 14, line 64 | cancel "Aedes" and substitute -- Aëdes -- |
| Col. 16, line 10 | cancel "Aedes" and substitute -- Aëdes -- |

UNITED STATES PATENT OFFICE
CERTIFICATE OF CORRECTION

Patent No. 4,026,934   Dated May 31, 1977

Inventor(s) Werner Daum et al.   Page 3 of 4

It is certified that error appears in the above-identified patent and that said Letters Patent are hereby corrected as shown below:

Col. 29, last compound   cancel "$(CH_2)_5\text{-}CO\text{-}O\text{-}CH_3$" 

and substitute

-- $(CH_2)_5\text{-}CO\text{-}O\text{-}CH_3$ --

Col. 37, compound 6   cancel "$CH_2\text{-}CH_2\text{-}N$
                                       |
                                      $CH_2$
                                       |
                                       N" and substitute -- $CH_2\text{-}CH_2\text{-}CH_2\text{-}N$
              |
              N  --

Col. 42, compound 15   raise "$(CH_2)_5$" to form

-- $(CH_2)_5\text{-}CO\text{-}NH\text{-}CH_3$ --

UNITED STATES PATENT OFFICE
CERTIFICATE OF CORRECTION

Patent No. 4,026,934　　　　　　　　　Dated May 31, 1977

Inventor(s) Werner Daum et al.　　　　　Page 4 of 4

It is certified that error appears in the above-identified patent and that said Letters Patent are hereby corrected as shown below:

Col. 44, line 4　　　　　cancel "Schull" and substitute -- Schüll --

Col. 49, line 34　　　　cancel "was" and substitute -- were --

Col. 50, line 25　　　　to far left of compound, insert -- (c) --

Signed and Sealed this thirtieth Day of August 1977

[SEAL]

Attest:

RUTH C. MASON
Attesting Officer

C. MARSHALL DANN
Commissioner of Patents and Trademarks